United States Patent
Shapiro (10) Patent No.: US 10,705,236 B2
(45) Date of Patent: Jul. 7, 2020

(54) METHOD FOR DETERMINING THE HYDRAULIC PERMEABILITY OF ROCKS IN A SUBSURFACE REGION

(71) Applicant: Freie Universitaet Berlin, Berlin (DE)

(72) Inventor: Serge Shapiro, Berlin (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 296 days.

(21) Appl. No.: 15/754,205

(22) PCT Filed: Jul. 21, 2016

(86) PCT No.: PCT/EP2016/067402
§ 371 (c)(1),
(2) Date: Feb. 21, 2018

(87) PCT Pub. No.: WO2017/032520
PCT Pub. Date: Mar. 2, 2017

(65) Prior Publication Data
US 2018/0252830 A1    Sep. 6, 2018

(30) Foreign Application Priority Data
Aug. 27, 2015    (DE) ........................ 10 2015 216 394

(51) Int. Cl.
*G01V 1/30*    (2006.01)
*G01N 33/24*    (2006.01)
(Continued)

(52) U.S. Cl.
CPC ............. *G01V 1/306* (2013.01); *G01N 15/08* (2013.01); *G01N 33/24* (2013.01); *G01V 1/282* (2013.01);
(Continued)

(58) Field of Classification Search
None
See application file for complete search history.

(56) References Cited

U.S. PATENT DOCUMENTS

| | | | |
|---|---|---|---|
| 4,926,394 A | 5/1990 | Doyen | |
| 5,193,059 A | 3/1993 | Tiab et al. | |

(Continued)

FOREIGN PATENT DOCUMENTS

| | | |
|---|---|---|
| WO | WO 98/34190 | 6/2009 |
| WO | WO 2009/070365 A1 | 6/2009 |
| WO | WO 2015/077581 A1 | 5/2015 |

OTHER PUBLICATIONS

S A Shapiro (Permeability dependency on stiff and compliant porosities: a model and some experimental examples, Published May 6, 2015, J. Geophys. Eng. 12 (2015) 376-385). (Year: 2015).*
(Continued)

*Primary Examiner* — Tung S Lau
(74) *Attorney, Agent, or Firm* — Gordon Rees Scully Mansukhani, LLP (57) ABSTRACT

An exemplary embodiment of the invention relates a method for determining hydraulic permeability of rocks in a subsurface region, the method comprising: in-situ measuring and/or calculating at least one of independent seismic velocities of rocks at different locations in said subsurface region; determining at least one lithological unit in said subsurface region based on the measured seismic velocities; for the at least one lithological unit, acquiring at least one rock sample at an at least one location of said subsurface region; measuring the rock-sample porosity and permeability as functions of stress; measuring and/or calculating of at least one of independent seismic velocities of said at least one rock sample as functions of stress; computing the stiff and compliant porosity of said at least one rock sample; computing numerical coefficients of a given analytical per-
(Continued)

```
┌─ Information Acquisition ─┐

Collection of Seismic Data on the subsurface target: Reflection Seismic,
Vertical Seismic Profiling, Cross-hole Tomography, Well logging    100
                            ↓
Identification and calculation of lithologic units of the reservoir    110
                            ↓
Acquisition of rock samples from the lithologic units    120
                            ↓
Additional information: e.g., stress, flow log, resistivity    130
``` meability model based on the stiff and compliant porosities; computing coefficients of a given analytical model of an elastic-compliance characteristic of the rock based on the stiff and compliant porosity; computing the stiff and compliant porosity for a plurality of other locations in said subsurface region; and computing the permeability of rocks belonging to said at least one lithological unit, for said at least one location in said subsurface region and for said plurality of other locations in said subsurface region.

14 Claims, 5 Drawing Sheets (51) Int. Cl.
 *G01N 15/08* (2006.01)
 *G01V 11/00* (2006.01)
 *G01V 1/28* (2006.01)
(52) U.S. Cl.
 CPC .............. *G01V 1/305* (2013.01); *G01V 11/00* (2013.01); *G01V 11/002* (2013.01); *G01V 2210/6244* (2013.01); *G01V 2210/6246* (2013.01)

(56) References Cited

U.S. PATENT DOCUMENTS

| | | | |
|---|---|---|---|
| 5,475,589 | A | 12/1995 | Armitage |
| 5,638,269 | A | 6/1997 | Fournier et al. |
| 6,381,543 | B1 | 4/2002 | Guerillot et al. |
| 7,679,993 | B2 | 3/2010 | Sayers |
| 8,175,807 | B2 | 5/2012 | Suarez-Rivera et al. |
| 8,243,549 | B2 | 8/2012 | Sayers |
| 8,688,425 | B2 | 4/2014 | Oppert et al. |
| 2014/0136117 | A1 | 5/2014 | Banian et al. |
| 2014/0372095 | A1 | 12/2014 | van der Zee et al. |
| 2015/0000903 | A1 | 1/2015 | Ly et al. |
| 2016/0138390 | A1* | 5/2016 | Arntsen .................. E21B 47/14 175/45 |
| 2016/0320504 | A1* | 11/2016 | Lindgaard .............. G01V 1/282 |

OTHER PUBLICATIONS

Axel Kaselow, et al.; "Stress Sensitivity of Elastic Moduli and Electrical Resistivity in Porous Rocks"; Nanjing Institute of Geophysical Prospecting and Institute of Physics Publishing; Journal of Geophysics and Engineering; Published Feb. 11, 2004; pp. 1-11.
Gary Mavko et al.; "The Rock Physics Handbook—Tools for Seismic Analysis in Porous Media"; Cambridge University Press (Stanford-Cambridge Program); (1998).
Serge A. Shapiro; "Fluid-Induced Seismicity"; Cambridge University Press, Cambridge (U.K.); (2015).
Serge A. Shapiro et al.; "Porosity and Elastic Anisotropy of Rocks Under Tectonic Stress and Pore-Pressure Changes"; Society of Exploration Geophysicists; vol. 70; No. 5; Sep.-Oct. 2005; pp. N27-N38.
S. A. Shapiro et al.; "Permeability Dependency on Stiff and Compliant Porosities: A Model and Some Experimental Examples"; Journal of Geophysics and Engineering; Sinopec Geophysical Research institute; (2015); pp. 376-385.
S. A. Shapiro et al; "Triggering of Seismicity by Pore-Pressure Perturbation: Permeability-Related Signatures of the Phenomenon", Pure and Applied Geophysics; (2003); pp. 1051-1066.
Robert W. Zimmerman et al.; "Compressibility of Porous Rocks"; Journal of Geophysical Research; vol. 91; No. B12; pp. 12,765-12,777; Nov. 10, 1986.
Serge A. Shapiro; "Elastic Piezodensitivity of Porous and Fractured Rock"; Geophysics; vol. 68; No. 2; Mar.-Apr. 2003; pp. 482-486.
S.A. Shapiro; "Method of Determining Hydraulic Permeability of Subsurface Rocks Using Seismic Data"; FR-Geophysik; Freie Universitaet Berlin, Berlin, Germany; Jul. 6, 2015.
International Search Report and Written Opinion dated Apr. 11, 2016 issued in PCT/EP2016/067402.

\* cited by examiner

METHOD FOR DETERMINING THE HYDRAULIC PERMEABILITY OF ROCKS IN A SUBSURFACE REGION

TECHNICAL FIELD

This invention relates generally to the field of geophysical exploration, geophysical data interpretation and processing, and geophysical reservoir characterization, and more specifically, to determining, computing, mapping and modelling transport properties of rocks (especially permeability and porosity of rocks) from seismic data.

The transport properties of rocks play an important role for development of underground reservoirs, for example in the oil and gas production, in construction of fluid or gas underground storages or wastes disposal systems, in production of water or geothermal energy.

BACKGROUND OF THE INVENTION

Accurate information on transport properties of rocks (especially on permeability and porosity) is important for optimizing various fluid-related geo-technical applications.

Existing methods for calculating transport properties from seismic data are described e.g. in US patents U.S. Pat. Nos. 4,926,394, 5,475,589, 5,638,269, 6,381,543, and U.S. Pat. No. 8,688,425. The existing methods deduce the rock permeability via statistical calibration or correlation of various seismic attributes with the permeability or by computing the permeability from a porosity value computed in turn from seismic data.

Such computations may sometimes take lithological factors like the clay content into account. Corresponding computational equations have a calibrating and/or correlative character.

Additionally, a method for calculating transport properties from seismic data is described in WO 2009/070365 A1. Here, the transport properties of rocks are computed from a rock sample 3D image segmented into compositional classes based on similarities in mineralogy, structure and spatial distribution. Then a mathematical model is selected that relates an effective (averaged) transport property or elastic property to the volume fractions of each compositional class.

Further, U.S. Pat. No. 8,175,807 B2 describes a method for estimating tectonic-origin elastic stresses in rocks.

WO 2015/077581 A1 describes a workflow for determining stresses and/or mechanical properties in anisotropic formations.

OBJECTIVE OF THE PRESENT INVENTION

An objective of the present invention is to provide a method for determining hydraulic permeability of rocks in a plurality of locations of a subsurface region between and/or away of boreholes with a high accuracy and with a high spatial resolution using data of non-invasive geophysical measurements.

BRIEF SUMMARY OF THE INVENTION

An embodiment of the invention relates to a method for determining hydraulic permeability of rocks in a subsurface region, the method comprising:
(1) in-situ measuring and/or calculating at least one of independent seismic velocities of rocks which are located at different locations in said subsurface region;
(2) determining at least one lithological unit in said subsurface region based on the measured seismic velocities;
(3) for the at least one lithological unit, acquiring at least one rock sample at an at least one location of said subsurface region;
(4) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;
(5) measuring the rock-sample permeability of said at least one rock sample as a function of effective pressure;
(6) measuring and/or calculating of at least one of independent seismic velocities of said at least one rock sample as a function of effective pressure and under in-situ fluid-saturation conditions;
(7) computing the stiff and compliant porosity of said at least one rock sample as a function of effective pressure, said computing being carried out on the basis of a given analytical porosity model and the porosity of said at least one rock sample as a function of effective pressure as measured in step 4;
(8) computing numerical coefficients of a given analytical permeability model based on the stiff and compliant porosities as determined in step 7 and on the permeability of said at least one rock sample as a function of effective pressure as measured in step 5;
(9) computing coefficients of a given analytical model of an elastic-compliance characteristic of the rock based on the stiff and compliant porosity as determined in step 7 and on seismic velocities of said at least one rock sample as a function of effective pressure as measured and/or calculated in step 6;
(10) computing the stiff and compliant porosity for a plurality of other locations in said subsurface region based on the seismic velocities of rocks in said subsurface region as measured in step 1, the stiff and compliant porosity as determined in step 7 and the coefficients determined in step 9;
(11) computing the permeability of rocks, which belong to said at least one lithological unit, for said at least one location in said subsurface region and for said plurality of other locations in said subsurface region, said computing being based on said stiff and compliant porosity of said at least one rock sample as a function of effective pressure as determined in step 7, the coefficients as determined in steps 8 and 9, and the stiff and compliant porosity for said plurality of other locations in said subsurface region as determined in step 10.

The method as described above provides with accurate results because on the one hand it takes the relations between the compliant and stiff porosities and the corresponding transport property into account, and on the other hand it takes the relation between the compliant and stiff porosities and the seismic properties into account.

Said at least one of independent seismic velocities of rocks is preferably the velocity of an independent seismic body wave, for instance the seismic primary P-wave (also known as seismic longitudinal wave in case of isotropic propagation media) or the seismic secondary S-wave (also known as the seismic shear wave in case of isotropic propagation media). The velocity of the independent seismic body wave may be measured or calculated.

In a preferred embodiment, a plurality of different lithological units may be determined in step 2. For each of the plurality of different lithological units at least one rock sample may be acquired. Steps 4 to 11 may be carried out for each of said plurality of different lithological units, and wherein the permeability of rocks may be computed for each of said plurality of different lithological units.

In a further preferred embodiment, said step 7 of computing the stiff and compliant porosity of said at least one rock sample may be carried out based on the following model:

$$\varphi = \varphi_s + \varphi_c$$

$$\varphi_s = \varphi^{s0} + \varphi^{s1}$$

$$\varphi^{s1}(P) = -(C^{drs} - C^{gr})P$$

$$\varphi_c(P) = \varphi^{c0} \exp(-\theta^c C^{drs} P)$$

$$\varphi(P) = \varphi^{s0} - (C^{drs} - C^{gr})P + \varphi^{c0} \exp(-\theta^c C^{drs} P)$$

wherein $\varphi$ designates the porosity,
wherein $\varphi_s$ designates the stiff porosity,
wherein $\varphi_c$ designates the compliant porosity,
wherein $\varphi^{c0}$ designates the compliant porosity in the unloaded rock, namely the undeformed compliant porosity of the rock under the zero effective pressure,
wherein $\varphi^{s0}$ designates the stiff porosity in the unloaded rock, namely the undeformed stiff porosity of the rock under the zero effective pressure,
wherein $\varphi^{s1}$ designates a stiff-porosity change caused by an application of the effective pressure to the rock,
wherein P designates the effective pressure,
wherein $\varphi(P)$, $\varphi_s(P)$, $\varphi_c(P)$, $\varphi^{s1}(P)$ designate the porosities denoted above of said at least one rock sample as functions of effective pressure, respectively,
wherein $C^{drs}$ designates the bulk compressibility of the drained rock containing undeformed stiff pores and closed compliant pores,
wherein $C^{gr}$ designates the bulk compressibility of the grain material of the rock, and
wherein the coefficient $\theta^c$ designates the stress sensitivity of the bulk compressibility of the drained rock.

In a further preferred embodiment, said step 8 of computing the numerical coefficients of said given analytical permeability model may be carried out based on the following permeability model:

$$k(P) = \Phi_s \varphi_s^{n_s}(P) + \Phi_c \varphi_c^{n_c}(P)$$

wherein k(P) designates the permeability of said at least one rock sample as a function of effective pressure,
wherein $\Phi_s$, $\Phi_c$, $n_s$, $n_c$ are the numerical coefficients of said analytical permeability model, and
wherein the porosities $\varphi_s(P)$, $\varphi_c(P)$ as functions of effective pressure are formulated in the preceding claim.

In a further preferred embodiment, said step 9 of computing the coefficients of said given analytical elastic-compliance-characteristic model may be carried out based on the following model:

$$\Lambda(P) = \Lambda^{rs} - \theta^{\Lambda s}(C^{drs} - C^{gr})P + \theta^{\Lambda c} \varphi^{c0} \exp(-\theta^c C^{drs} P)$$

wherein $\Lambda(P)$ designates said elastic-compliance characteristic of said at least one rock sample as a function of effective pressure,
wherein the coefficient $\Lambda^{rs}$ designates said elastic-compliance characteristic of said at least one rock sample under conditions of closed compliant pores and undeformed stiff pores,
wherein the coefficient $\theta^{\Lambda s}$ designates the sensitivity of said elastic-compliance characteristic to changes of the stiff porosity,
wherein the coefficient $\theta^{\Lambda c}$ designates the sensitivity of said elastic-compliance characteristic to changes of the compliant porosity,
wherein $C^{drs}$ designates the bulk compressibility of the drained rock containing undeformed stiff pores and closed compliant pores,
wherein $C^{gr}$ designates the bulk compressibility of the grain material of the rock,
wherein the coefficient $\theta^c$ designates the stress sensitivity of the bulk compressibility of the drained rock,
wherein $\varphi^{c0}$ designates the compliant porosity in the unloaded rock, namely the undeformed compliant porosity of the rock under the zero effective pressure,
wherein said elastic-compliance characteristic of the rock is defined as a power-law, polynomial, or another positive monotonic increasing function of one or more of the following variables:

$$1/V_P^2,$$

$$1/V_S^2,$$

$$1/(V_P^2 - 4V_S^2/3),$$

wherein $V_P$ designates the velocity of seismic longitudinal waves, and
wherein $V_S$ designates the velocity of seismic shear waves.

In a further preferred embodiment, said step 10 of computing the stiff and compliant porosity in said plurality of locations belonging to a given lithologic unit (where said elastic-compliance characteristic may have been preliminary computed based on seismic velocities as described above) may be carried out based on the following model:

$$\Lambda_{min} = \Lambda^{rs} - \theta^{\Lambda s} \varphi^{s1}$$

$$\Lambda(\bar{r}) - \Lambda_{min} = \theta^{\Lambda c} \varphi_c(\bar{r})$$

$$\varphi_s(\bar{r}) = \varphi^{s0} + \varphi^{s1}$$

$$\varphi_c(\bar{r}) = (\Lambda(\bar{r}) - \Lambda_{min})/\theta^{\Lambda c}$$

wherein $\Lambda_{min}$ is the minimum value of said elastic-compliance characteristic computed in the given lithologic unit,
wherein $\Lambda(\bar{r})$ is the value of said elastic-compliance characteristic computed at the location $\bar{r}$, and wherein $\varphi_s(\bar{r})$ and $\varphi_c(\bar{r})$ are said stiff and compliant porosities at the location $\bar{r}$, respectively.

In a further preferred embodiment, said step 11 of computing the permeability of said rocks at said plurality of locations $\bar{r}$ may be carried out based on the following equation:

$$k(\bar{r}) = \Phi_s \varphi_s^{n_s}(\bar{r}) + \Phi_c \varphi_c^{n_c}(\bar{r})$$

wherein $k(\bar{r})$ designates said permeability of said rock at the location $\bar{r}$, and
wherein $\Phi_s$, $\Phi_c$, $n_s$, $n_c$ are the numerical coefficients of said analytical permeability model formulated as defined above.

In a further preferred embodiment, said step 6 of measuring of seismic velocity of said at least one rock sample as a function of effective pressure may be carried out for at least two independent seismic velocities $V_P$ and $V_S$.

Said step 9 of computing the coefficients of said given analytical elastic-compliance-characteristic model may be carried out for at least two independent elastic-compliance characteristics based on the following model:

$$\Lambda_1(P) = \Lambda_1^{rs} - \theta^{\Lambda s1}(C^{drs} - C^{gr})P + \theta^{\Lambda c1} \varphi^{c0} \exp(-\theta^c C^{drs} P)$$

$$\Lambda_2(P) = \Lambda_2^{rs} - \theta^{\Lambda s2}(C^{drs} - C^{gr})P + \theta^{\Lambda c2} \varphi^{c0} \exp(-\theta^c C^{drs} P)$$

wherein $\Lambda_1(P)$ and $\Lambda_2(P)$ designate said two independent elastic-compliance characteristics of said at least one rock sample as functions of effective pressure, respectively,
wherein the coefficients $\Lambda_1^{rs}$ and $\Lambda_2^{rs}$ designate said independent elastic-compliance characteristics of said at least one rock sample under conditions of closed compliant pores and undeformed stiff pores, respectively,
wherein the coefficient $\theta^{\Lambda s1}$ and $\theta^{\Lambda s2}$ designate the sensitivities of said two independent elastic-compliance characteristics to changes of the stiff porosity, respectively,
wherein the coefficient $\theta^{\Lambda c1}$ and $\theta^{\Lambda c2}$ designate the sensitivities of said two independent elastic-compliance characteristics to changes of the compliant porosity, respectively,
wherein $C^{drs}$ designates the bulk compressibility of the drained rock containing undeformed stiff pores and closed compliant pores,
wherein $C^{gr}$ designates the bulk compressibility of the grain material of the rock,
wherein the coefficient $\varphi^c$ designates the stress sensitivity of the bulk compressibility of the drained rock, and
wherein $\varphi^{c0}$ designates the compliant porosity in the unloaded rock, namely the undeformed compliant porosity of the rock under the zero effective pressure.

Said two independent elastic-compliance characteristics of the rock may be defined as independent power-law, polynomial, or other positive monotonic increasing functions of one or more of independent variables equal to the squared reciprocal said independent seismic velocities.

Said step 10 of computing the stiff and compliant porosity in said plurality of locations r belonging to a given lithologic unit (where said at least two independent elastic-compliance characteristics may have been preliminary computed based on seismic velocities as described above) may be carried out based on solving the following equation system:

$$\Lambda_1(\bar{r}) = \Lambda^{rs1} - \theta^{\Lambda s1}(\varphi_s(\bar{r}) - \varphi^{s0}) + \theta^{\Lambda c1}\varphi_c(\bar{r})$$

$$\Lambda_2(\bar{r}) = \Lambda^{rs2} - \theta^{\Lambda s2}(\varphi_s(\bar{r}) - \varphi^{s0}) + \theta^{\Lambda c2}\varphi_c(\bar{r})$$

In a further preferred embodiment, said step 1 may comprise or may be replaced by the determining at least one lithological unit in said subsurface region based on seismic travel-times and seismic waveforms.

In a further preferred embodiment, said step 2 may comprise or may be replaced by the in-situ determining the directions of the maximum and/or minimum longitudinal seismic velocities and/or the directions of the polarisations of shear seismic waves with maximum and/or minimum seismic velocities.

In a further preferred embodiment, for any lithologic unit from said plurality of the lithologic units in the case of $\Phi_s \ll \Phi_c$ a qualitative conclusion about the directivity of the maximum and/or minimum principal component of the permeability tensor may be made in accordance with the directions of the maximum and/or minimum longitudinal seismic velocities and/or the directions of polarisations of shear seismic waves with maximum and/or minimum velocities, respectively, wherein $\Phi_s$, $\Phi_c$, are the numerical coefficients of said analytical permeability model may be formulated as described above.

A further embodiment of the invention relates to a method determining hydraulic permeability of rocks in a subsurface region, the method comprising:
(1a) determining at least one lithological unit in said subsurface region based on seismic travel-times and seismic waveforms;
(2a) in-situ determining the directions of the maximum and/or minimum longitudinal seismic velocities and/or the directions of the polarisations of shear seismic waves with maximum and/or minimum seismic velocities;
(3a) for the at least one lithological unit, acquiring at least one rock sample at an at least one location of said subsurface region;
(4a) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;
(5a) measuring the rock-sample permeability of said at least one rock sample as a function of effective pressure;
(6a) computing the stiff and compliant porosity of said at least one rock sample as a function of effective pressure, said computing being carried out on the basis of a given analytical porosity model and the porosity of said at least one rock sample as a function of effective pressure as measured in step 4a;
(7a) computing numerical coefficients of a given analytical permeability model based on the stiff and compliant porosities as determined in step 6a and on the permeability of said at least one rock sample as a function of effective pressure as measured in step 5a;
(8a) for any lithologic unit from said plurality of lithologic units in the case of $\Phi_s \ll \Phi_c$ making a qualitative conclusion about the directivity of the maximum and/or minimum principal component of the permeability tensor in accordance with the directions of the maximum and/or minimum longitudinal seismic velocities and/or the directions of polarisations of shear seismic waves with maximum and/or minimum velocities, respectively,
wherein $\Phi_s$, $\Phi_c$, are the numerical coefficients of said analytical permeability model having the form $$k(P) = \Phi_s \varphi_s^{n_s}(P) + \Phi_c \varphi_c^{n_c}(P)$$

wherein $k(P)$ designates the permeability of said at least one rock sample as a function of effective pressure,
wherein $n_s$, $n_c$ are the numerical coefficients of said analytical permeability model, and
wherein the porosities $\varphi_s(P)$, $\varphi_c(P)$ as functions of effective pressure are formulated as follows:

$$\varphi = \varphi_s + \varphi_c$$

$$\varphi_s = \varphi^{s0} + \varphi^{s1}$$

$$\varphi^{s1}(P) = -(C^{drs} - C^{gr})P$$

$$\varphi_c(P) = \varphi^{c0} \exp(-\theta^c C^{drs} P)$$

$$\varphi(P) = \varphi^{s0} - (C^{drs} - C^{gr})P + \varphi^{c0} \exp(-\theta^c C^{drs} P)$$

wherein $\varphi$ designates the porosity,
wherein $\varphi_s$ designates the stiff porosity,
wherein $\varphi_c$ designates the compliant porosity,
wherein $\varphi^{c0}$ designates the compliant porosity in the unloaded rock, namely the undeformed compliant porosity of the rock under the zero effective pressure,
wherein $\varphi^{s0}$ designates the stiff porosity in the unloaded rock, namely the undeformed stiff porosity of the rock under the zero effective pressure,
wherein $\varphi^{s1}$ designates a stiff-porosity change caused by an application of the effective pressure to the rock,
wherein P designates the effective pressure, wherein $\varphi(P)$, $\varphi_s(P)$, $\varphi_c(P)$, $\varphi^{s1}(P)$ designate the porosities denoted above of said at least one rock sample as functions of effective pressure, respectively, wherein $C^{drs}$ designates the bulk compressibility of the drained rock containing undeformed stiff pores and closed compliant pores, wherein $C^{gr}$ designates the bulk compressibility of the grain material of the rock, and wherein the coefficient $\theta^c$ designates the stress sensitivity of the bulk compressibility of the drained rock.

A further embodiment of the invention relates to a method for determining hydraulic permeability of rocks in a subsurface region, the method comprising: in-situ measuring and/or calculating at least one of independent seismic velocities of rocks which are located at different locations in said subsurface region; determining at least one lithological unit in said subsurface region based on the measured seismic velocities; for the at least one lithological unit, acquiring at least one rock sample at an at least one location of said subsurface region; measuring the rock-sample porosity and permeability; measuring and/or calculating of at least one of independent seismic velocities of said at least one rock sample; computing the stiff and compliant porosity of said at least one rock sample; computing numerical coefficients of a given analytical permeability model based on the stiff and compliant porosities; computing coefficients of a given analytical model of an elastic-compliance characteristic of the rock based on the stiff and compliant porosity; computing the stiff and compliant porosity for a plurality of other locations in said subsurface region; and computing the permeability of rocks, which belong to said at least one lithological unit, for said at least one location in said subsurface region and for said plurality of other locations in said subsurface region.

The method steps 1-11 of claims 1-9 are based on the seismic velocities of the rocks or rock samples. Alternatively, the method steps can be based on the acoustic impedance of the rock or rock samples.

Accordingly, a further embodiment of the invention relates to a method for determining hydraulic permeability of rocks in a subsurface region, the method comprising:

(1b) in-situ measuring and/or calculating of the acoustic impedance being the product of the gravitational density with the seismic P-wave velocity of rocks which are located at different locations in said subsurface region;

(2b) determining at least one lithological unit in said subsurface region based on the measured acoustic impedances;

(3b) for the at least one lithological unit, acquiring at least one rock sample at an at least one location of said subsurface region;

(4b) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;

(5b) measuring the rock-sample permeability of said at least one rock sample as a function of effective pressure;

(6b) measuring and/or calculating of the acoustic impedance, as defined in step 1, of said at least one rock sample as a function of effective pressure and under in-situ fluid-saturation conditions;

(7b) computing the stiff and compliant porosity of said at least one rock sample as a function of effective pressure, said computing being carried out on the basis of a given analytical porosity model and the porosity of said at least one rock sample as a function of effective pressure as measured in step 4;

(8b) computing numerical coefficients of a given analytical permeability model based on the stiff and compliant porosities as determined in step 7 and on the permeability of said at least one rock sample as a function of effective pressure as measured in step 5;

(9b) computing coefficients of a given analytical model of an elastic-compliance characteristic of the rock based on the stiff and compliant porosity as determined in step 7 and on acoustic impedance of said at least one rock sample as a function of effective pressure as measured in step 6;

(10b) computing the stiff and compliant porosity for a plurality of other locations in said subsurface region based on the acoustic impedances in rocks in said subsurface region as measured in step 1, the stiff and compliant porosity as determined in step 7 and the coefficients determined in step 9; and (11b) computing the permeability of rocks, which belong to said at least one lithological unit, for said at least one location in said subsurface region and for said plurality of other locations in said subsurface region, said computing being based on said stiff and compliant porosity of said at least one rock sample as a function of effective pressure as determined in step 7, the coefficients as determined in steps 8 and 9, and the stiff and compliant porosity for said plurality of other locations in said subsurface region as determined in step 10.

In the embodiment described above, the acoustic impedance is defined as the product of the gravitational density with the seismic P-wave velocity of rocks which are located at different locations in the subsurface region. Alternatively, the acoustic impedance may be defined as the product of the gravitational density with the seismic S-wave velocity of rocks which are located at different locations in the subsurface region.

Accordingly, a further embodiment of the invention relates to a method for determining hydraulic permeability of rocks in a subsurface region, the method comprising:

(1b) in-situ measuring and/or calculating of the acoustic impedance being the product of the gravitational density with the seismic S-wave velocity of rocks which are located at different locations in said subsurface region;

(2b) determining at least one lithological unit in said subsurface region based on the measured acoustic impedances;

(3b) for the at least one lithological unit, acquiring at least one rock sample at an at least one location of said subsurface region;

(4b) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;

(5b) measuring the rock-sample permeability of said at least one rock sample as a function of effective pressure;

(6b) measuring and/or calculating of the acoustic impedance, as defined in step 1, of said at least one rock sample as a function of effective pressure and under in-situ fluid-saturation conditions;

(7b) computing the stiff and compliant porosity of said at least one rock sample as a function of effective pressure, said computing being carried out on the basis of a given analytical porosity model and the porosity of said at least one rock sample as a function of effective pressure as measured in step 4;

(8b) computing numerical coefficients of a given analytical permeability model based on the stiff and compliant porosities as determined in step 7 and on the permeability of said at least one rock sample as a function of effective pressure as measured in step 5;

(9b) computing coefficients of a given analytical model of an elastic-compliance characteristic of the rock based on the stiff and compliant porosity as determined in step 7 and on acoustic impedance of said at least one rock sample as a function of effective pressure as measured in step 6;

(10b) computing the stiff and compliant porosity for a plurality of other locations in said subsurface region based on the acoustic impedances in rocks in said subsurface region as measured in step 1, the stiff and compliant porosity as determined in step 7 and the coefficients determined in step 9; and (11b) computing the permeability of rocks, which belong to said at least one lithological unit, for said at least one location in said subsurface region and for said plurality of other locations in said subsurface region, said computing being based on said stiff and compliant porosity of said at least one rock sample as a function of effective pressure as determined in step 7, the coefficients as determined in steps 8 and 9, and the stiff and compliant porosity for said plurality of other locations in said subsurface region as determined in step 10.

Furthermore, the method may include the step of combining acoustic impedances of seismic P-waves and S-waves. For instance, step (1b) may include in-situ measuring and/or calculating of the acoustic impedance being the product of the gravitational density with the seismic P-wave velocity of rocks which are located at different locations in said subsurface region;

in-situ measuring and/or calculating of the acoustic impedance being the product of the gravitational density with the seismic S-wave velocity of said rocks; and combining (e.g. by calculating an average value) the P-wave related acoustic impedance and the S-wave related acoustic impedance in order to form a combined acoustic impedance.

In the latter case, steps 2b-11b may be carried out based on the combined acoustic impedance.

In a further embodiment of the invention, the method may include determining a plurality of different lithological units in above mentioned steps 2 or 2b, by carrying out the steps of acquiring for each of the plurality of different lithological units at least one rock sample and carrying out above mentioned steps 3-11 or steps 3b to 11b for each of said plurality of different lithological units.

BRIEF DESCRIPTION OF THE DRAWINGS

In order that the manner in which the above-recited and other advantages of the invention are obtained will be readily understood, a more particular description of the invention briefly described above will be rendered by reference to specific embodiments thereof which are illustrated in the appended figures. Understanding that these figures depict only typical embodiments of the invention and are therefore not to be considered to be limiting of its scope, the invention will be described and explained with additional specificity and detail by the use of the accompanying drawings in which.

DETAILED DESCRIPTION OF THE PREFERRED EMBODIMENT

Specific embodiments of determining permeability from seismic data will now be described in an exemplary fashion with reference to the accompanying Figures.

It will be readily understood that the present invention, as generally described herein, could vary in a wide range. Thus, the following more detailed description of the exemplary embodiments of the present invention, is not intended to limit the scope of the invention, as claimed, but is merely representative of presently preferred embodiments of the invention.

Figure 1:
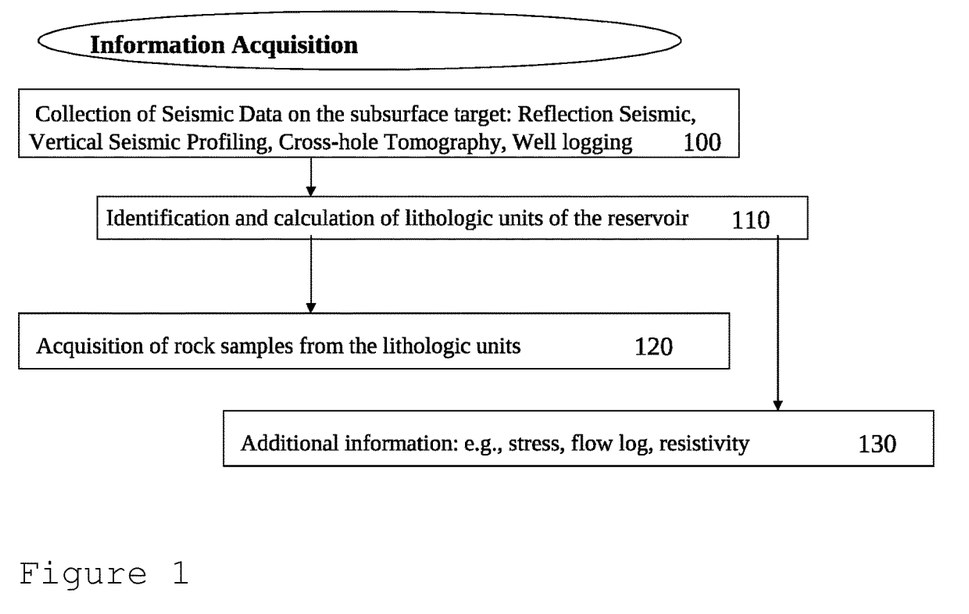
FIG. 1 is a flowchart of exemplary processes for the information acquisition.

In general, estimating permeability of rocks from seismic data relates to a method for determining elastic properties of rocks (these are products of rock gravitational densities with squares of seismic velocities or, equivalently, elastic stiffnesses or, equivalently, their reciprocals, called elastic compliances, or equivalently acoustic impedances of seismic P- and S-waves being equal to the products of P- and S-wave velocities with the gravitational density, respectively, or equivalently seismic P- and S-wave velocities, or equivalently their reciprocals called seismic slowness, or equivalently various functions of these quantities) using reflection seismic data or equivalently, vertical seismic profiling (VSP) data or equivalently, seismic tomography data or equivalently, an interpolation of borehole logging data, or equivalently any combination of such methods (process 100 on FIG. 1).

The method may further include application of seismic inversion techniques for computing elastic properties from the seismic data (processes 100 on FIG. 1).

The method may further include determining elastic properties of rocks using sonic logging techniques (processes 100 on FIG. 1).

The method may further include determining porosities of rocks using wire-line logging techniques (processes 100 on FIG. 1).

The method may further include determining rock densities using gravimetrical field measurements, borehole measurements, laboratory measurements and/or an interpolation of measured density values.

The method may further include calculation of lithologic units in subsurface locations (process 110 on FIG. 1).

A lithologic unit is identified by a combination of one or more of elastic properties and/or seismic traveltimes and/or seismic waveforms obtained from seismic data
- with meaningful available seismic attributes (e.g., instantaneous frequency, Amplitude versus Offset property, image coherency),
- with meaningful available logging information (e.g., elastic properties, lithology, electric resistivity, gamma-log data, elastic anisotropy, fracturing, fluid type), and
- with available core information (e.g., mineralogical composition, clay content, pore space morphology, lithology, elastic properties, permeability, 2-D and 3-D images of rock samples, etc.)

The lithologic units represent meaningful geologic facies of interest. Technique that may be used to derive lithologic units from seismic data are known. Examples are described by Oppert et al. (2004, Sand/Shale Discrimination in Mixed-Impedance Reservoirs Using AVO Attributes, SEG, Expanded Abstracts 23 (1), pp. 1495-1498) and U.S. Pat. No. 6,950,786 (Sonneland et al.).

The method may further include collection of rock samples (process 120 on FIG. 1) and of additional information (e.g., geological, geophysical, petrophysical, geochemical and tectonic information) from the lithologic units (process 130 on FIG. 1).

Figure 2:
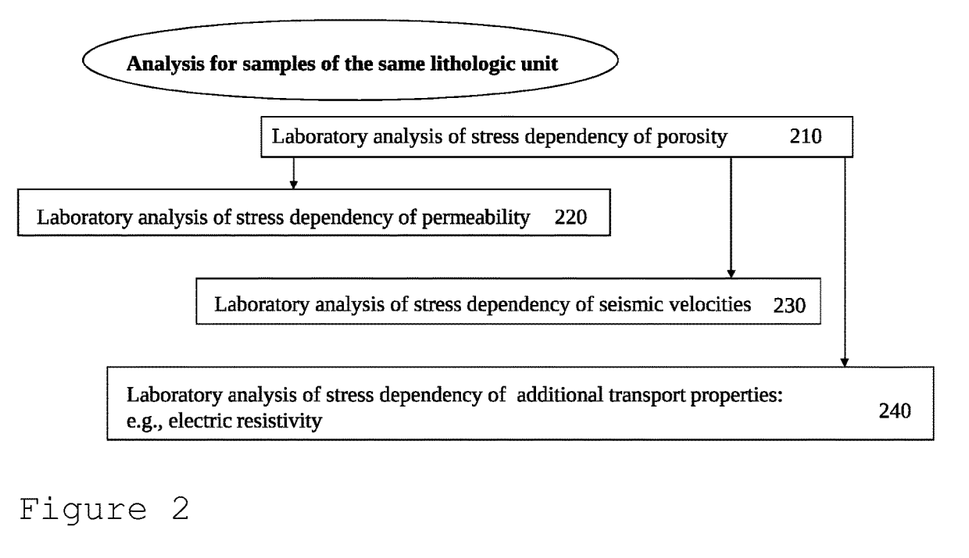
FIG. 2 is a flowchart of an exemplary process of the analysis for samples of the same lithologic unit.

The method may further include determining stress dependencies of porosities of rocks and of permeabilities of rocks and of elastic properties of rocks using techniques of measurements on rock samples in laboratory (Processes 210-240, FIG. 2). Processes 210-240 are applied to rocks representing lithologic units of interest in the subsurface.

Figure 3:
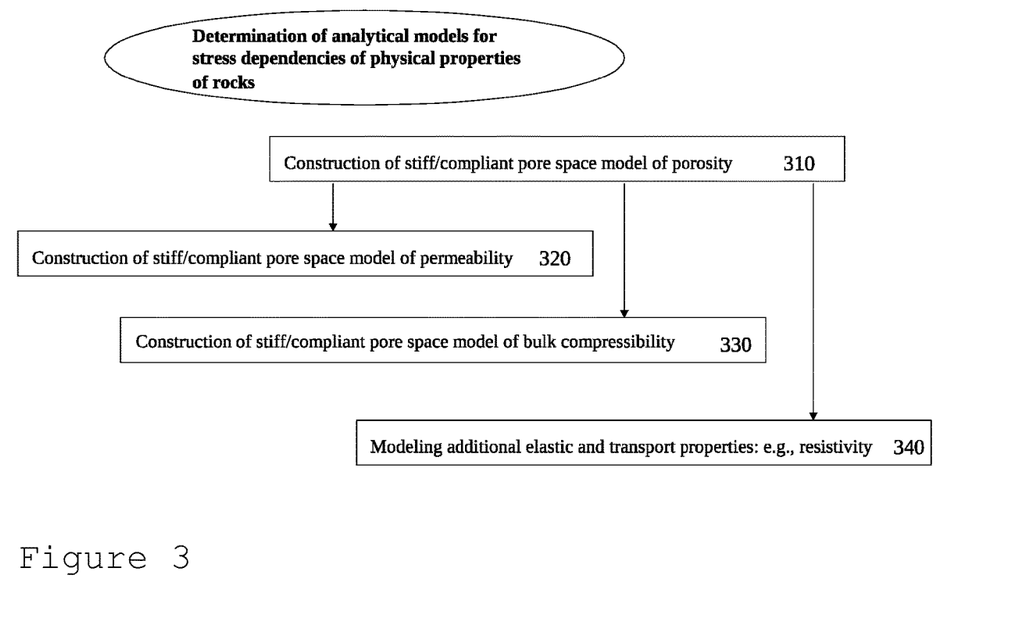
FIG. 3 is a flowchart of an exemplary process (called modelling) of the determination of analytical models for stress dependencies of physical properties of rocks.

The method may further include determination of analytical models (mathematical relations) describing the stress dependency of the porosity, the stress dependency of the permeability and the stress dependency of elastic properties (processes 310, 320 and 330 on FIG. 3).

The method may also include modelling of additional transport or other physical properties of rocks as functions of applied stresses (process 340 on FIG. 3). These analytical models are used to determine the type of the stress dependency of rocks permeability supported by compliant and stiff parts of the pore space of rocks of the lithologic units. The analytical models are not of any correlative or calibrating character. They are based on solid physical understanding of the micromechanical factors determining stress dependencies of rock properties. The construction way of the models is described below in detail.

The stress dependency of elastic moduli of drained rocks is mainly controlled by deformations of the compliant pore space (very thin cracks and vicinities of grain contacts; see e.g., Zimmerman et al., 1986; and Shapiro, 2003).

For a laboratory experiment with a rock sample, in the first approximation, the reservoir rock is assumed to be elastically and hydraulically isotropic. Anisotropy of physical properties of rocks may be introduced into consideration too.

The rock sample may be jacketed, i.e., it is possible to independently apply the confining pressure $P_c$ and the pore pressure $P_p$ to the outer boundary of the sample and to the surface of its connected void space (composed of pores, cracks, grain contact vicinities etc.), respectively.

The permeability and porosity can be approximately considered as functions of the effective pressure $P=P_c-P_p$ (also called differential pressure). Under non-hydrostatic conditions the confining pressure $P_c$ is equal to the arithmetic average of the three principal tectonic elastic stresses.

Figure 6:
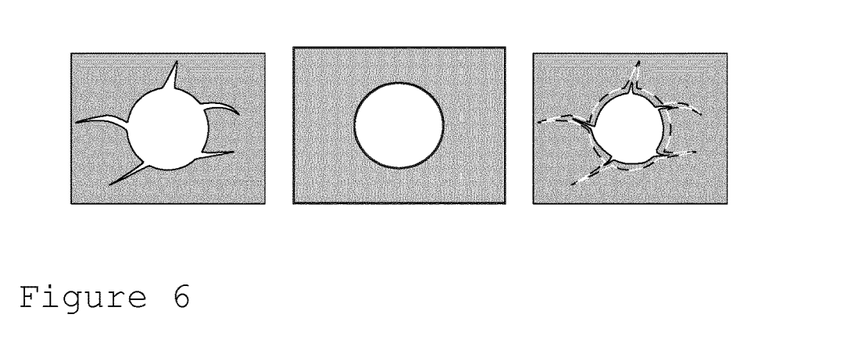
FIG. 6 is an idealized sketch of the pore space: in the unloaded state the pore space consists of stiff pores and compliant pores (on the left); it is in contrast to the reference state (in the middle) where the pore space consists only of undeformed stiff pores; in the loaded case (on the right) both stiff and compliant pores are deformed due to an applied effective pressure (this Figure is modified after Shapiro and Kaselow, 2005).

It is possible to separate the connected porosity $\varphi$ (see the sketch on FIG. 6) into the compliant porosity $\varphi_c$ and the stiff porosity $\varphi_s$:

$$\varphi=\varphi_s+\varphi_c \quad (1)$$

Shapiro et al., (2015) proposed to separate contributions of these two parts of the porosity to the permeability.

The porosity $\varphi$ changes due to changes of the loading stresses ($P_c$; $P_p$). Shapiro (2003) and Shapiro and Kaselow (2005) separate the total connected stiff porosity $\varphi_s$ into two parts:

$$\varphi_s=\varphi^{s0}+\varphi^{s1}, \quad (2)$$

where $\varphi^{s1}$ is a change of the stiff porosity $\varphi_s$ due to changing loading stress, and $\varphi^{s0}$ is the stiff porosity in the absence of the load, i.e., P=0. The geometric model of the pore space is not specified. It remains general and arbitrary. The compliant and the stiff porosity are only defined in respect to their reaction on the load of the rock.

The compliant pore space includes usually very thin cracks and grain contact vicinities. The compliant porosity is the one which will close up when P reaches the order of a few tens of MPa. Such a closing load corresponds to voids with an aspect ratio (a relationship between the minimum and maximum dimensions of a pore) less than 0.01 (see Zimmerman et al., 1986). Such voids are usually addressed as cracks.

The stiff porosity, $\varphi_s=\varphi^{s0}+\varphi^{s1}$ is supported by more or less equidimensional (oval-like or worm-like, i.e., approximately equidimensional in their stiff cross-sections) voids. Such voids are frequently addressed as pores. Oval- or worm-like residuals of closed fractures and cracks can also belong to the stiff porosity. The aspect ratio of such pores (in their minimum cross-sections) is typically larger than $0.1$.

Usually the relative changes of the stiff porosity, $\varphi^{s1}/\varphi^{s0}$, are small in the range of moderate loadings (P is below 100 MPa). In contrast, the relative changes of the compliant porosity $(\varphi_c-\varphi^{c0})/\varphi^{c0}$ can be of the order of 1 ($\varphi^{c0}$ denotes the compliant porosity in the unloaded state, P=0). Both quantities, $\varphi_c$ and $\varphi^{c0}$, have usually very small values. As a general rule, (e.g., in porous sandstones) they are much smaller than $\varphi^{s0}$.

For example, in porous sandstones realistic orders of magnitude of these quantities are $\varphi^{s0}0.1$, $|\varphi^{s1}|=0.01$, and both, $\varphi_c$ and $\varphi^{c0}$ can be less than or of the order of 0.01.

The "drained and stiff" state of the rock is defined as a drained rock with the porosity given by the stiff porosity in the unloaded state, $\varphi=\varphi^{s0}$. Physical properties of the rock in the reference state are defined by the superscript "drs" standing for "drained and stiff".

Shapiro, (2003) and Shapiro and Kaselow, (2005) have shown that stiff and compliant porosities have the following load dependencies:

$$\varphi^{s1}(P) = -(C^{drs} - C^{gr})P \quad (3)$$

$$\varphi_c(P) = \varphi^{c0} \exp(-\theta^c C^{drs} P) \quad (4)$$

Here $C^{drs}$ and $C^{gr}$ represent the bulk compressibility of the "drained and stiff" rock and the bulk compressibility of the grain material of the rock, respectively. Here $\theta^c$ is a rock property called piezo-sensitivity. It is the stress sensitivity of the bulk compressibility of drained rock.

The stress-dependent porosity takes the following form:

$$\varphi(P) = \varphi^{s0} - (C^{drs} - C^{gr})P + \varphi^{c0} \exp(-\theta^c C^{drs} P) \quad (5)$$

Shapiro, (2003) and Shapiro and Kaselow, (2005) have shown that an elastic property Λ (including, a velocity of a seismic wave, an acoustic impedance, a rock stiffness or a rock compliance) can be approximately represented as follows:

$$\Lambda(P) = \Lambda^{rs} - \theta^{\Lambda s}(C^{drs} - C^{gr})P + \theta^{\Lambda c}\varphi^{c0} \exp(-\theta^c C^{drs} P) \quad (6)$$

where $\Lambda^{rs}$ denotes the physical property Λ (e.g., an elastic compliance) in the reference state of the rock. The reference state of a rock is defined as the rock under the in-situ saturation condition with the porosity given by the stiff porosity in the unloaded state, $\varphi = \varphi^{s0}$. Physical properties of the rock in the reference state are defined by the superscript "rs" standing for "reference state".

Furthermore, coefficients $\theta^{\Lambda s}$ and $\theta^{\Lambda c}$ are physical properties of rocks. These properties can be defined for example by laboratory measurements. Kaselow and Shapiro (2004) proposed the same type of equation for electrical resistivity of porous and fractured rocks.

Figure 7:
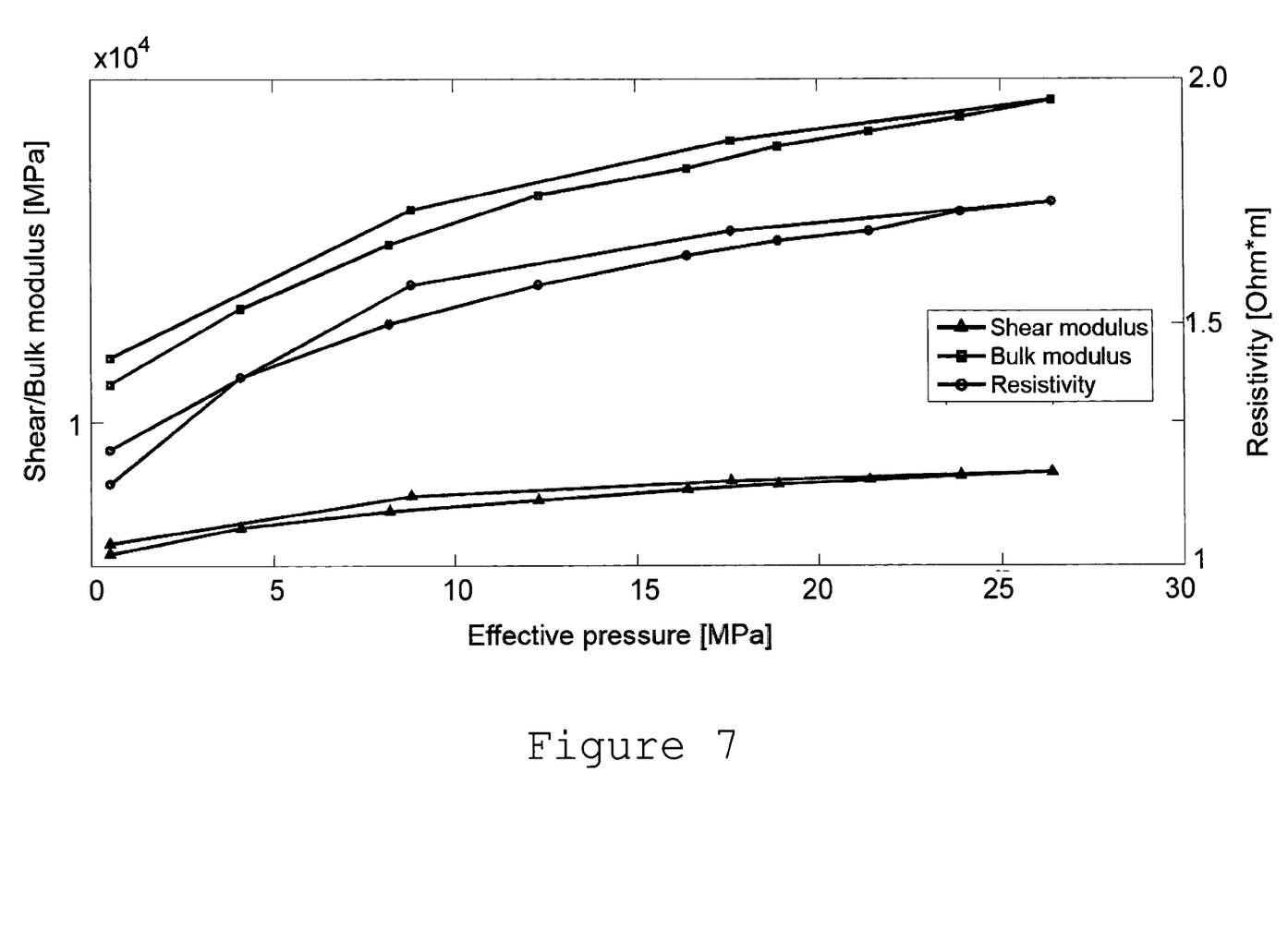
FIG. 7 is an example graph illustrating dependencies of the bulk and shear moduli and of specific resistivity for a rock sample on effective pressure for a terrigenous sample "B" from an oil reservoir, Perm, in Russia; the upper branches of the curves correspond to the load release; these are measurements at effective pressure equal approx. to 1, 8, and 18 MPa (this Figure is taken from Shapiro et al., 2015)
Figure 8:
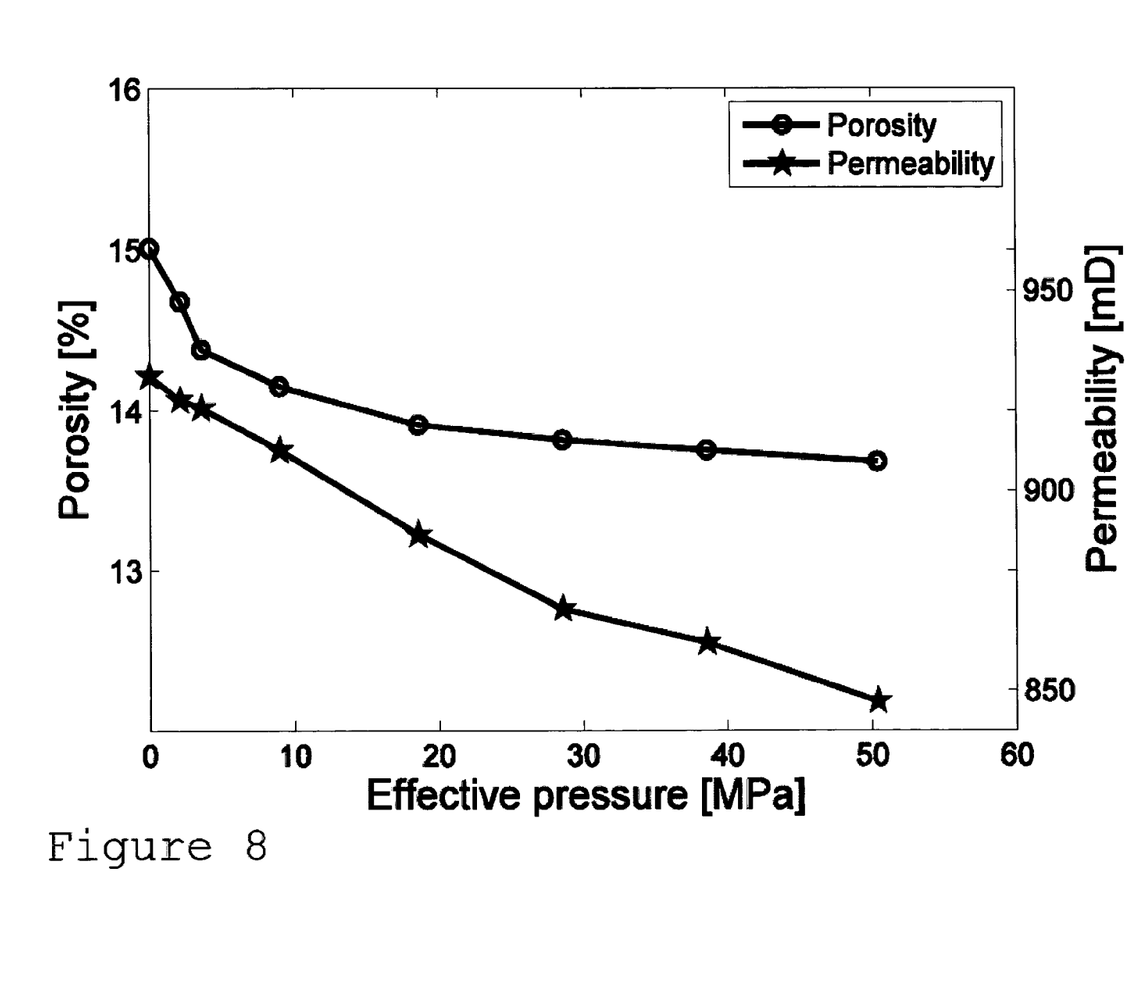
FIG. 8 is an example graph illustrating stress dependencies of the porosity and the permeability for a rock sample (porosity and permeability are shown as functions of the effective pressure for a sample of sandstone "A" from an oil reservoir at Perm, in Russia; this Figure is taken from Shapiro et al., 2015).

FIG. 7 shows stress dependencies of several elastic and electrical properties of a rock sample B from a carboniferous (Visean age) clastic oil reservoir of the Russian Perm region. All these dependencies can be well described by equation (6). In the low-to-moderate range of loads the third term on the right-hand side of equation (6) is significantly larger than the second one. This corresponds to curved parts of lines shown in FIG. 7. Stress dependencies of these properties are mainly controlled by the third term on the right-hand side which is defined by the compliant porosity.

A functional relation of the permeability of a rock to its stiff and compliant porosities of the following general form must be further used:

$$k = f(\Phi_s \varphi_s; \Phi_c \varphi_c) \quad (7)$$

where $f$ denotes a general functional dependency and the stiff and compliant porosities are taken with different weighting factors $\Phi_s$ and $\Phi_c$, respectively. Shapiro et al., (2015) shown that the following two analytical models describe well the functional relation (7):

$$k = (\Phi_s \varphi_s + \Phi_c \varphi_c)^n \quad (8)$$

$$k = \Phi_s \varphi_s^{n_s} + \Phi_c \varphi_c^{n_c} \quad (9)$$

The weighting factors $\Phi_s$ and $\Phi_c$, and the exponents $n_s$ and $n_c$, or alternatively n, can be defined from laboratory experiments on load dependence of the permeability, of the porosity and of elastic properties, as described for example below.

According to the models (8) and (9) the stress dependence of the permeability is given by the following functions, respectively:

$$k(P) = [\Phi_s(\varphi^{s0} - (C^{drs} - C^{gr})P) + \Phi_c \varphi^{c0} \exp(-\theta^c C^{drs} P)]^n \quad (10)$$

$$k(P) = \Phi_s[(\varphi^{s0} - (C^{drs} - C^{gr})P)]^{n_s} + \Phi_c[\varphi^{c0} \exp(-\theta^c C^{drs} P)]^{n_c} \quad (11)$$

If the permeability is controlled by a stiff porosity only then $\Phi_c = 0$. For example, this can be the case for high-porosity sandstones where compliant pores are mainly confined to grain contacts and do not significantly contribute to permeability which is controlled by stiff pore throats. In this case $$k(P) \approx k_0(1 - (C^{drs} - C^{gr})P/\varphi^{s0})^{n_s} \approx k_0(1 - n_s(C^{drs} - C^{gr})P/\varphi^{s0}), \quad (12)$$

where $k_0$ is the permeability at P=0 and the last approximation is made for the case of small stiff-porosity changes in the range of applied loads. In this last case the permeability dependency on P can be approximated by a linear function.

If the permeability change is mainly controlled by the compliant porosity, then in equation (11) the term $(C^{drs} - C^{gr})P/\varphi^{s0}$ is small in respect to 1 and the following approximation can be applied:

$$k(P) \approx k_{rs} + \Phi_c[\varphi^{c0}]^{n_c} \exp(-\theta^c n_c C^{drs} P), \quad (13)$$

where $k_{rs}$ is the permeability of the reference state of the rock. This equation may correspond, for instance, to fractured carbonates, where compliant voids (fractures) provide the main conduits between isolated vugs. Moreover, if stiff pores do not provide any significant contribution to the permeability at all, then $\Phi_s = 0$. This yields:

$$k(P) \approx k_0 \exp(-\theta^c n_c C^{drs} P). \quad (14)$$

The determination of analytical models (mathematical relations) describing the stress dependency of the porosity, the stress dependency of the permeability and the stress dependency of elastic properties correspond to processes 310, 320 and 330 on FIG. 3. These processes are applied to samples of a given lithologic unit. The process 310 (FIG. 3) includes computations of coefficients $\varphi^{s0}$, $C^{drs} - C^{gr}$, $\varphi^{c0}$, $\theta^c \cdot C^{drs}$ using equation (5) and using the measured stress dependency of the porosity of the rock of a given lithologic unit (this measurement is the process 210 on FIG. 2).

The determination of analytical models includes further computations of the coefficients $\Lambda^{rs}$, $\theta^{\Lambda s}$ and $\theta^{\Lambda c}$ using the measured stress dependency of an elastic-compliance characteristic of the rock corresponding to equation (6).

This step corresponds to the processes 330-340 of the FIG. 3.

In one or several embodiments of the method the elastic-compliance characteristic of the rock may be chosen to be equal to one of the following quantities: $1/V_P^2$, $1/V_S^2$, or $1/(V_P^2 - 4V_S^2/3)$, wherein $V_P$ designates the velocity of seismic longitudinal waves, and $V_S$ designates the velocity of seismic shear waves. The longitudinal and shear seismic waves can propagate independently from each other. Any two of the quantities $1/V_P^2$, $1/V_S^2$, or $1/(V_P^2 - 4V_S^2/3)$ are functions of independent seismic velocities.

In one or several embodiments of the method the elastic-compliance characteristic of the rock may be chosen to be equal to the undrained bulk compressibility of the rock. It is directly equal to the quantity $1/[(V_P^2 - 4V_S^2/3)\rho]$ measured/or computed for a fluid-saturated undrained rock, wherein $\rho$ is the gravitational density of this rock.

The measurements of the density and seismic velocity belong to known well-established approaches of the laboratory rock physics and of the seismic exploration.

In one or several embodiments of the method the elastic-compliance characteristic of the rock may be chosen to be equal to the drained bulk compressibility $C^{dr}$ of the rock. It is directly equal to the quantity $1/[(V_P^2 - 4V_S^2/3)\rho_{dr}]$ measured/or computed for a drained (usually, room-dry) rock, wherein $\rho_{dr}$ is the gravitational density of this rock.

In this case the following particular form of equation (6) is used in the process 330 of the FIG. 3:

$$C^{dr}(P)=C^{drs}-\theta^{Cs}(C^{drs}-C^{gr})P+C^{drs}\theta^c\varphi^{c0}\exp(-\theta^c C^{drs}P), \quad (15)$$

wherein the coefficient $\theta^{Cs}$ designates the sensitivity of the drained bulk compressibility of the rock to changes of the stiff porosity. In respect to the equation (6) the equation (15) contains one coefficient less to be determined and provides a direct possibility of estimating the coefficient $C^{drs}$.

In one or several embodiments of the method the drained bulk compressibility may be computed from the undrained bulk compressibility using approaches based on the theory of Poroelasticity like the Gassmann equation or the fluid-substitution equation (Mavko et al, 1998).

The determination of analytical models in the steps 330-340 (FIG. 3) may include computations of coefficients of analytical formulas for two or more elastic properties from their measured stress dependencies and corresponding forms of the equation (6):

$$\Lambda_1(P)=\Lambda_1^{rs}-\theta^{\Lambda s1}(C^{drs}-C^{gr})P+\theta^{\Lambda c1}\varphi^{c0}\exp(-\theta^c C^{drs}P) \quad (16)$$

$$\Lambda_2(P)=\Lambda_2^{rs}-\theta^{\Lambda s2}(C^{drs}-C^{gr})P+\theta^{\Lambda c2}\varphi^{c0}\exp(-\theta^c C^{drs}P) \quad (17)$$

wherein $\Lambda_1(P)$ and $\Lambda_2(P)$ designate two independent elastic-compliance characteristics of the rock sample as functions of effective pressure, respectively. The coefficients $\Lambda_1^{rs}$ and $\Lambda_2^{rs}$ designate these elastic-compliance characteristics under conditions of closed compliant pores and undeformed stiff pores (the reference state of the rock), respectively. The coefficients $\theta^{\Lambda s1}$ and $\theta^{\Lambda s2}$ designate the sensitivities of the elastic-compliance characteristics to changes of the stiff porosity, respectively. The coefficient $\theta^{\Lambda c1}$ and $\theta^{\Lambda c2}$ designate the sensitivities of the elastic-compliance characteristics to changes of the compliant porosity, respectively.

Figure 5:
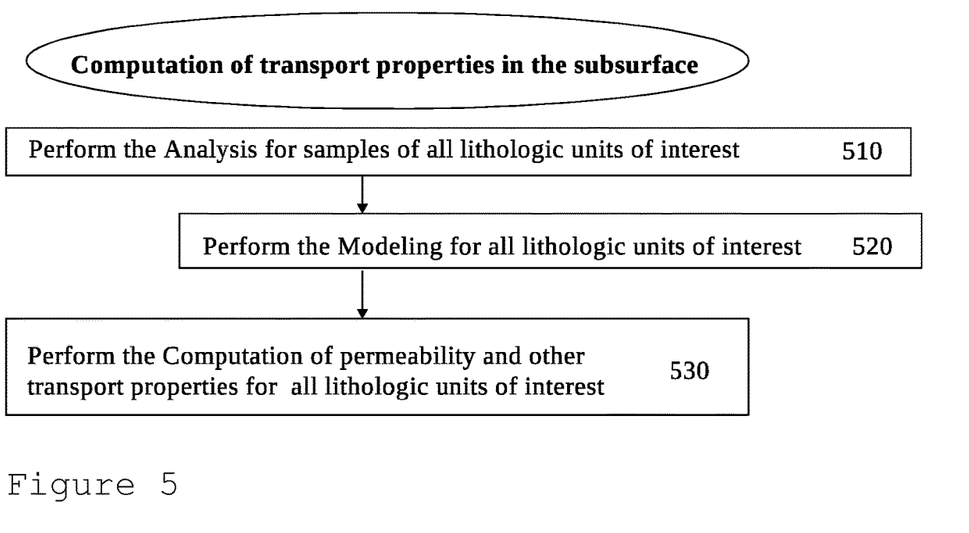
FIG. 5 is a flowchart of an exemplary process of the computation of transport properties in the subsurface.

The determination of analytical models may include computations of one or more coefficients $\Phi_s$, $\Phi_c$, $n_s$, $n_c$, and/or n, using the equations (10) and/or (11). This step corresponds to the process 320 of the FIG. 3. The processes 310-340 are performed for a given lithologic unit. They are repeated for rock samples of other lithologic units (see processes 510 and 520, FIG. 5).

Figure 4:
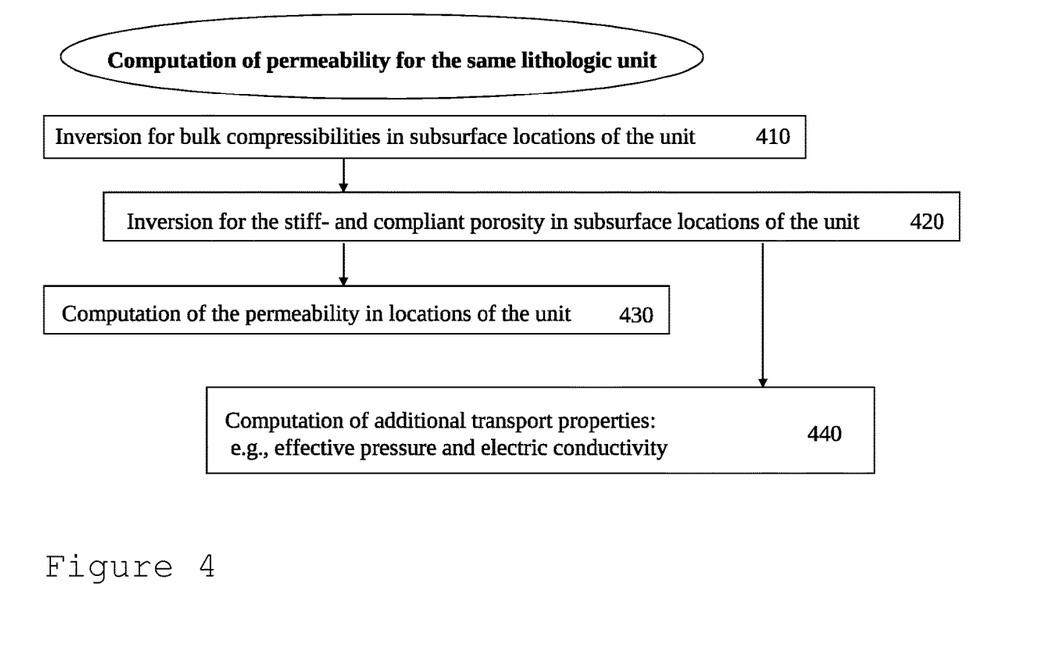
FIG. 4 is a flowchart of an exemplary process of the computation of permeability for the same lithologic unit.

The computation of transport properties for locations of the reservoir belonging to the same lithologic unit includes processes 410-440 shown in FIG. 4. Using seismic data the drained bulk compressibility may be computed in reservoir locations of the lithologic unit. This corresponds to the process 410 in FIG. 4. Such operations belong to known well-established approaches of the processing of seismic data.

In one or several embodiments of the method the computations of the processes 420-440 may be done in the following way based on equation (15). Assume that the quantity $C_{min}^{dr}$ is the minimum drained compressibility in the lithologic unit. It may be assumed that this quantity corresponds to the bulk compressibility of the rock with closed compliant porosity. This corresponds to the following mathematical relation including the coefficients introduced above:

$$C_{min}^{dr}=C^{drs}-\theta^{Cs}\varphi^{s1}. \quad (18)$$

In the process 420 (FIG. 4) the quantities $\varphi^{s1}$, $\varphi_s$, and $\varphi_c$ are computed. Firstly, using the relation (18) and the coefficients $C^{drs}$ and $\theta^{Cs}$ computed in the processes 310-340 the quantity $\varphi^{s1}$ is computed. This quantity represents the change of the stiff porosity in respect to its unloaded value.

The unloaded stiff porosity $\varphi^{s0}$ has been already defined in 310-340. Using for example equation (1) the stiff porosity $\varphi_s$ can be found.

The differences between the drained compressibility in a location of the lithologic unit on one hand and the value of $C_{min}^{dr}$ on the other hand corresponds approximately to the following relation:

$$C^{dr}-C_{min}^{dr}=\theta^c\varphi_c. \quad (19)$$

Using this relation and the coefficient $\theta^c$ estimated in the processes 310-340 the quantity $\varphi_c$ is estimated.

In one or several embodiments of the method the computations of the processes 420-440 may be done in the following way based on equations (16) and (17). In a given lithologic unit, at any point $\bar{r}$ of interest two independent elastic-compliance characteristics $\Lambda_1(\bar{r})$ and $\Lambda_2(\bar{r})$ are measured or computed from seismic data. These operations belong to known well-established approaches of the processing of seismic data. In one or several embodiments of the method these characteristics may be equal to squared reciprocal velocities of seismic longitudinal and shear waves. Then, in the process 420 (FIG. 4) the quantities $\varphi_s$, and $\varphi_c$ are computed from solving the following system of equations:

$$\Lambda_1(\bar{r})=\Lambda^{rs1}-\theta^{\Lambda s1}(\varphi_s(\bar{r})-\varphi^{s0})+\theta^{\Lambda c1}\varphi_c(\bar{r}),$$

$$\Lambda_2(\bar{r})=\Lambda^{rs2}-\theta^{\Lambda s2}(\varphi_s(\bar{r})-\varphi^{s0})+\theta^{\Lambda c2}\varphi_c(\bar{r}),$$

wherein the coefficients $\varphi^{s0}$, $C^{drs}$ and $\theta^{Cs}$ have been computed in the previous processes 310-340.

In the process 430 (FIG. 4) the permeability may be estimated using relations (8) or (9) and using the coefficients and quantities estimated in the processes 310-340 and 410-420.

In the process 440 additional transport parameters may be calculated. For example, the effective pressure in-situ may be calculated using the quantities and coefficients found in the processes 310-440 and the following relation:

$$P=\frac{\ln(\varphi^{c0}/\varphi_c)}{\theta^c C^{drs}} \quad (20)$$

Also the electric resistivity can be found using the obtained porosities and the Archie law (see Kaselow and Shapiro, 2004).

In one or several embodiments of the method the process 430 may be replaced and/or the process 440 may be complemented by the following. Firstly the process 410 is completed or replaced by the in-situ determining the directions of the maximum and/or minimum longitudinal seismic velocities and/or the directions of the polarisations of shear seismic waves with maximum and/or minimum seismic velocities in the given lithologic unit and/or at a given location. These operations belong to known well-established approaches of the processing of seismic data. Then, in the case of $\Phi_s<<\Phi_c$ (these coefficients are being determined in the process 320) a qualitative conclusion about the directivity of the maximum and/or minimum principal component of the permeability tensor is made in accordance with the directions of the maximum and/or minimum longitudinal seismic velocities and/or the directions of polarisations of shear seismic waves with maximum and/or minimum velocities, respectively.

In the processes 510-530 (FIG. 5) the processes 210-440 are repeated for other lithologic units of interest in the subsurface. The method may be applied to any subsurface region including the over- and underburden of the reservoir.

In summary, exemplary embodiments of the invention relate inter alia to a method of characterizing hydraulic permeability of subsurface rocks that includes measuring seismic velocities of rocks, measuring rock-sample porosity as a function of stress, measuring rock-sample permeability as a function of stress, measuring rock-sample seismic velocities as functions of stress, computing coefficients of an analytical porosity model in terms of the stiff and compliant porosity, computing coefficients of an analytical permeability model in terms of the stiff and compliant porosity, computing coefficients of an analytical bulk-compressibility model in terms of the stiff and compliant porosity, computing the stiff and compliant porosity from seismic velocities of rocks in the subsurface, computing the permeability of rocks in the subsurface using the coefficients of the analytical permeability model in terms of the stiff and compliant porosity, and characterize more properties of the subsurface rocks, for example, the effective pore pressure and/or electric conductivity, using the analytical models of porosity, permeability and bulk compressibility.

REFERENCES

Kaselow, A. and Shapiro, S. A. (2004), "Stress sensitivity of elastic moduli and electrical resistivity in porous rocks", Journal of Geophysics and Engineering, 1:1-11.

Mavko, G., Mukerji, T., and Dvorkin, J. (1998), "The Rock Physics Handbook: Tools for seismic analysis in porous media", Cambridge Univ. Press.

Shapiro, S. A. (2015), "Fluid-Induced Seismicity", Cambridge University Press, Cambridge (U.K.).

Shapiro, S. A. and Kaselow, A. (2005), "Porosity and elastic anisotropy of rocks under tectonic stress and pore-pressure changes", Geophysics, 70:N27-N38, doi:10.1190/1.2073884.

Shapiro, S. A., Khizhniak, G. P., Plotnikov, V. V., Niemann, R., Ilyushin, P. Y., and Galkin, S. V. (2015), "Permeability dependency on stiff and compliant porosities: a model and some experimental examples", Journal of Geophysics and Engineering, 12: 376-385, doi:10.1088/1742-2132/12/3/376J.

Shapiro, S. A., Patzig, R., Rothert, E., and Rindschwentner, J. (2003), "Triggering of microseismicity due to pore-pressure perturbation: Permeability related signatures of the phenomenon", PAGEOPH, 160:1051-1066.

Zimmerman R W, Somerton W H and King M S 1986 Compressibility of porous rocks J. Geophys. Res. 91 12765-77.

The invention claimed is:

1. A method for determining hydraulic permeability of rocks in a subsurface region, the method comprising:
   (1) in-situ measuring and/or calculating at least one of independent seismic velocities of rocks which are located at different locations in said subsurface region;
   (2) determining at least one lithological unit in said subsurface region based on the measured seismic velocities;
   (3) for the at least one lithological unit, acquiring at least one rock sample at an at least one location of said subsurface region;
   (4) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;
   (5) measuring the rock-sample permeability of said at least one rock sample as a function of effective pressure;
   (6) measuring and/or calculating of at least one of independent seismic velocities of said at least one rock sample as a function of effective pressure and under in-situ fluid-saturation conditions;
   (7) computing the stiff and compliant porosity of said at least one rock sample as a function of effective pressure, said computing being carried out on the basis of a given analytical porosity model and the porosity of said at least one rock sample as a function of effective pressure as measured in step 4;
   (8) computing numerical coefficients of a given analytical permeability model based on the stiff and compliant porosities as determined in step 7 and on the permeability of said at least one rock sample as a function of effective pressure as measured in step 5;
   (9) computing coefficients of a given analytical model of an elastic-compliance characteristic of the rock based on the stiff and compliant porosity as determined in step 7 and on seismic velocities of said at least one rock sample as a function of effective pressure as measured in step 6;
   (10) computing the stiff and compliant porosity for a plurality of other locations in said subsurface region based on the seismic velocities of rocks in said subsurface region as measured in step 1, the stiff and compliant porosity as determined in step 7 and the coefficients determined in step 9; and
   (11) computing the permeability of rocks, which belong to said at least one lithological unit, for said at least one location in said subsurface region and for said plurality of other locations in said subsurface region, said computing being based on said stiff and compliant porosity of said at least one rock sample as a function of effective pressure as determined in step 7, the coefficients as determined in steps 8 and 9, and the stiff and compliant porosity for said plurality of other locations in said subsurface region as determined in step 10.

2. The method according to claim 1, wherein a plurality of different lithological units are determined in step 2, for each of the plurality of different lithological units at least one rock sample is acquired and steps 4 to 11 are carried out for each of said plurality of different lithological units and the permeability of rocks is computed for each of said plurality of different lithological units.

3. The method according to claim 1, wherein said step 7 of computing the stiff and compliant porosity of said at least one rock sample is carried out based on the following model:

$$\varphi = \varphi_s + \varphi_c$$

$$\varphi_s = \varphi^{s0} + \varphi^{s1}$$

$$\varphi^{s1}(P) = -(C^{drs} - C^{gr})P$$

$$\varphi_c(P) = \varphi^{c0} \exp(-\theta^c C^{drs} P)$$

$$\varphi(P) = \varphi^{s0} - (C^{drs} - C^{gr})P + \varphi^{c0} \exp(-\theta^c C^{drs} P)$$

wherein $\varphi$ designates the porosity,
wherein $\varphi_s$ designates the stiff porosity, wherein $\varphi_c$ designates the compliant porosity, wherein $\varphi^{c0}$ designates the compliant porosity in the unloaded rock, namely the undeformed compliant porosity of the rock under the zero effective pressure, wherein $\varphi^{s0}$ designates the stiff porosity in the unloaded rock, namely the undeformed stiff porosity of the rock under the zero effective pressure, wherein $\varphi^{s1}$ designates a stiff-porosity change caused by an application of the effective pressure to the rock, wherein P designates the effective pressure, wherein $\varphi(P)$, $\varphi_s(P)$, $\varphi_c(P)$, $\varphi^{s1}(P)$ designate the porosities denoted above of said at least one rock sample as functions of effective pressure, respectively, wherein $C^{drs}$ designates the bulk compressibility of the drained rock containing undeformed stiff pores and closed compliant pores, wherein $C^{gr}$ designates the bulk compressibility of the grain material of the rock, and wherein the coefficient $\theta^c$ designates the stress sensitivity of the bulk compressibility of the drained rock.

4. The method according to claim 1, wherein said step 8 of computing the numerical coefficients of said given analytical permeability model is carried out based on the following permeability model:

$$k(P)=\Phi_s\varphi_s^{n_s}(P)+\Phi_c\varphi_c^{n_c}(P)$$

wherein k(P) designates the permeability of said at least one rock sample as a function of effective pressure, wherein $\Phi_s$, $\Phi_c$, $n_s$, $n_c$ are the numerical coefficients of said analytical permeability model, and wherein the porosities $\varphi_s(P)$, $\varphi_c(P)$ as functions of effective pressure are formulated in the preceding claim.

5. The method according to claim 1, wherein said step 9 of computing the coefficients of said given analytical elastic-compliance-characteristic model is carried out based on the following model:

$$\Lambda(P)=\Lambda^{rs}-\theta^{\Lambda s}(C^{drs}-C^{gr})P+\theta^{\Lambda c}\varphi^{c0}\exp(-\theta^c C^{drs}P)$$

wherein $\Lambda(P)$ designates said elastic-compliance characteristic of said at least one rock sample as a function of effective pressure, wherein the coefficient $\Lambda^{rs}$ designates said elastic-compliance characteristic of said at least one rock sample under conditions of closed compliant pores and undeformed stiff pores, wherein the coefficient $\theta^{\Lambda s}$ designates the sensitivity of said elastic-compliance characteristic to changes of the stiff porosity, wherein the coefficient $\theta^{\Lambda c}$ designates the sensitivity of said elastic-compliance characteristic to changes of the compliant porosity, wherein $C^{drs}$ designates the bulk compressibility of the drained rock containing undeformed stiff pores and closed compliant pores, wherein $C^{gr}$ designates the bulk compressibility of the grain material of the rock, wherein the coefficient $\theta^c$ designates the stress sensitivity of the bulk compressibility of the drained rock, wherein $\varphi^{c0}$ designates the compliant porosity in the unloaded rock, namely the undeformed compliant porosity of the rock under the zero effective pressure, wherein said elastic-compliance characteristic of the rock is defined as a power-law, polynomial, or another positive monotonic increasing function of one or more of the following variables:

$1/V_P^2$, $1/V_S^2$, $1/(V_P^2-4V_S^2/3)$, wherein $V_P$ designates the velocity of seismic longitudinal waves, and wherein $V_S$ designates the velocity of seismic shear waves.

6. The method according to claim 1, wherein said step 10 of computing the stiff and compliant porosity in said plurality of locations belonging to a given lithologic unit, where said elastic-compliance characteristic may have been preliminary computed based on seismic velocities as described in claim 5, is carried out based on the following model:

$$\Lambda_{min}=\Lambda^{rs}-\theta^{\Lambda s}\varphi^{s1}$$

$$\Lambda(\bar{r})-\Lambda_{min}=\theta^{\Lambda c}\varphi_c(\bar{r})$$

$$\varphi_s(\bar{r})=\varphi^{s0}+\varphi^{s1}$$

$$\varphi_c(\bar{r})=(\Lambda(\bar{r})-\Lambda_{min})/\theta^{\Lambda c}$$

wherein $\Lambda_{min}$ is the minimum value of said elastic-compliance characteristic computed in the given lithologic unit, wherein $\Lambda(\bar{r})$ is the value of said elastic-compliance characteristic computed at the location $\bar{r}$, and wherein $\varphi_s(\bar{r})$ and $\varphi_c(\bar{r})$ are said stiff and compliant porosities at the location $\bar{r}$, respectively.

7. The method according to claim 1 wherein a plurality of different lithological units are determined in step 2, for each of the plurality of different lithological units at least one rock sample is acquired and steps 3 to 11 are carried out for each of said plurality of different lithological units and the permeability of rocks is computed for each of said plurality of different lithological units.

8. The method according to claim 1 wherein said at least one of independent seismic velocities of rocks is defined by the velocity of an independent seismic body wave, preferably the seismic primary P-wave or the seismic secondary S-wave.

9. The method according to claim 4, wherein said step 11 of computing the permeability of said rocks at said plurality of locations r is carried out based on the following equation:

$$k(\bar{r})=\Phi_s\varphi_s^{n_s}(\bar{r})+\Phi_c\varphi_c^{n_c}(\bar{r})$$

wherein $k(\bar{r})$ designates said permeability of said rock at the location $\bar{r}$, and wherein $\Phi_s$, $\Phi_c$, $n_s$, $n_c$ are the numerical coefficients of said analytical permeability model formulated in the claim 4.

10. The method according to claim 4, wherein (1) said step 1 also comprises or is replaced by the determining at least one lithological unit in said subsurface region based on seismic travel-times and seismic waveforms;

(2) said step 2 also comprises or is replaced by the in-situ determining the directions of the maximum and/or minimum longitudinal seismic velocities and/or the directions of the polarisations of shear seismic waves with maximum and/or minimum seismic velocities;

(3) for any lithologic unit from said plurality of the lithologic units in the case of $\Phi_s \ll \Phi_c$ a qualitative conclusion about the directivity of the maximum and/or minimum principal component of the permeability tensor is made in accordance with the directions of the maximum and/or minimum longitudinal seismic velocities and/or the directions of polarisations of shear seismic waves with maximum and/or minimum velocities, respectively, wherein $\Phi_s$, $\Phi_c$, are the numerical coefficients of said analytical permeability model formulated in claim 4.

11. The method according to claim 5, wherein said step 6 of measuring of seismic velocity of said at least one rock sample as a functions of effective pressure is carried out for at least two independent seismic velocities $V_P$ and $V_S$, wherein said step 9 of computing the coefficients of said given analytical elastic-compliance-characteristic model is carried out for at least two independent elastic-compliance characteristics based on the following model:

$$\Lambda_1(P)=\Lambda_1{}^{rs}-\theta^{\Lambda s1}(C^{drs}-C^{gr})P+\theta^{\Lambda c1}\varphi^{c0}\exp(-\theta^c C^{drs}P)$$

$$\Lambda_2(P)=\Lambda_2{}^{rs}-\theta^{\Lambda s2}(C^{drs}-C^{gr})P+\theta^{\Lambda c2}\varphi^{c0}\exp(-\theta^c C^{drs}P)$$

wherein $\Lambda_1(P)$ and $\Lambda_2(P)$ designate said two independent elastic-compliance characteristics of said at least one rock sample as functions of effective pressure, respectively, wherein the coefficients $\Lambda_1{}^{rs}$ and $\Lambda_2{}^{rs}$ designate said independent elastic-compliance characteristics of said at least one rock sample under conditions of closed compliant pores and undeformed stiff pores, respectively, wherein the coefficient $\theta^{\Lambda s1}$ and $\theta^{\Lambda s2}$ designate the sensitivities of said two independent elastic-compliance characteristics to changes of the stiff porosity, respectively, wherein the coefficient $\theta^{\Lambda c1}$ and $\theta^{\Lambda c2}$ designate the sensitivities of said two independent elastic-compliance characteristics to changes of the compliant porosity, respectively, wherein $C^{drs}$ designates the bulk compressibility of the drained rock containing undeformed stiff pores and closed compliant pores, wherein $C^{gr}$ designates the bulk compressibility of the grain material of the rock, wherein the coefficient $\theta^c$ designates the stress sensitivity of the bulk compressibility of the drained rock, wherein $\varphi^{c0}$ designates the compliant porosity in the unloaded rock, namely the undeformed compliant porosity of the rock under the zero effective pressure, wherein said two independent elastic-compliance characteristics of the rock are defined as independent power-law, polynomial, or other positive monotonic increasing functions of one or more of independent variables equal to the squared reciprocal said independent seismic velocities, wherein said step 10 of computing the stiff and compliant porosity in said plurality of locations $\bar{r}$ belonging to a given lithologic unit, where said at least two independent elastic-compliance characteristics have been preliminary computed based on seismic velocities as described in claim 5, is carried out based on solving the following equation system:

$$\Lambda_1(\bar{r})=\Lambda^{rs1}-\theta^{\Lambda s1}(\varphi_s(\bar{r})-\varphi^{s0})+\theta^{\Lambda c1}\varphi_c(\bar{r})$$

$$\Lambda_2(\bar{r})=\Lambda^{rs2}-\theta^{\Lambda s2}(\varphi_s(\bar{r})-\varphi^{s0})+\theta^{\Lambda c2}\varphi_c(\bar{r}).$$

12. A method for determining hydraulic permeability of rocks in a subsurface region, the method comprising:

(1a) determining at least one lithological unit in said subsurface region based on seismic travel-times and seismic waveforms;

(2a) in-situ determining the directions of the maximum and/or minimum longitudinal seismic velocities and/or the directions of the polarisations of shear seismic waves with maximum and/or minimum seismic velocities;

(3a) for the at least one lithological unit, acquiring at least one rock sample at an at least one location of said subsurface region;

(4a) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;

(5a) measuring the rock-sample permeability of said at least one rock sample as a function of effective pressure;

(6a) computing the stiff and compliant porosity of said at least one rock sample as a function of effective pressure, said computing being carried out on the basis of a given analytical porosity model and the porosity of said at least one rock sample as a function of effective pressure as measured in step 4a;

(7a) computing numerical coefficients of a given analytical permeability model based on the stiff and compliant porosities as determined in step 6a and on the permeability of said at least one rock sample as a function of effective pressure as measured in step 5a;

(8a) for any lithologic unit from said plurality of lithologic units in the case of $\Phi_s \ll \Phi_c$ making a qualitative conclusion about the directivity of the maximum and/or minimum principal component of the permeability tensor in accordance with the directions of the maximum and/or minimum longitudinal seismic velocities and/or the directions of polarisations of shear seismic waves with maximum and/or minimum velocities, respectively, wherein $\Phi_s$, $\Phi_c$, are the numerical coefficients of said analytical permeability model having the form $$k(P)=\Phi_s \varphi_s{}^{n_s}(P)+\Phi_c \varphi_c{}^{n_c}(P)$$

wherein k(P) designates the permeability of said at least one rock sample as a function of effective pressure, wherein $n_s$, $n_c$ are the numerical coefficients of said analytical permeability model, and wherein the porosities $\varphi_s$ (P), $\varphi_c$ (P) as functions of effective pressure are formulated as follows:

$$\varphi=\varphi_s+\varphi_c$$

$$\varphi_s=\varphi^{s0}+\varphi^{s1}$$

$$\varphi^{s1}(P)=-(C^{drs}-C^{gr})P$$

$$\varphi_c(P)=\varphi^{c0}\exp(-\theta^c C^{drs}P)$$

$$\varphi(P)=\varphi^{s0}-(C^{drs}-C^{gr})P+\varphi^{c0}\exp(-\theta^c C^{drs}P)$$

wherein $\varphi$ designates the porosity, wherein $\varphi_s$ designates the stiff porosity, wherein $\varphi_c$ designates the compliant porosity, wherein $\varphi^{c0}$ designates the compliant porosity in the unloaded rock, namely the undeformed compliant porosity of the rock under the zero effective pressure, wherein $\varphi^{s0}$ designates the stiff porosity in the unloaded rock, namely the undeformed stiff porosity of the rock under the zero effective pressure, wherein $\varphi^{s1}$ designates a stiff-porosity change caused by an application of the effective pressure to the rock, wherein P designates the effective pressure, wherein $\varphi(P)$, $\varphi_s(P)$, $\varphi_c(P)$, $\varphi^{s1}(P)$ designate the porosities denoted above of said at least one rock sample as functions of effective pressure, respectively, wherein $C^{drs}$ designates the bulk compressibility of the drained rock containing undeformed stiff pores and closed compliant pores, wherein $C^{gr}$ designates the bulk compressibility of the grain material of the rock, and wherein the coefficient $\theta^c$ designates the stress sensitivity of the bulk compressibility of the drained rock.

13. A method for determining hydraulic permeability of rocks in a subsurface region, the method comprising:
(1b) in-situ measuring and/or calculating of the acoustic impedance which is defined by the product of the gravitational density with the seismic P-wave velocity of rocks which are located at different locations in said subsurface region, by the product of the gravitational density with the seismic S-wave velocity of rocks which are located at different locations in said subsurface region, or by the result of a function that combines the acoustic impedances which have been calculated with respect to seismic P-waves and S-waves;
(2b) determining at least one lithological unit in said subsurface region based on the measured acoustic impedances;
(3b) for the at least one lithological unit, acquiring at least one rock sample at an at least one location of said subsurface region;
(4b) measuring the rock-sample porosity of said at least one rock sample as a function of the effective pressure, wherein the effective pressure is defined to be equal to the difference between, on the one hand, the confining pressure being equal to the arithmetic average of the three principal elastic stresses applied to the outer boundary of said rock sample and, on the other hand, the pore pressure acting in the pore space of said rock sample;
(5b) measuring the rock-sample permeability of said at least one rock sample as a function of effective pressure;
(6b) measuring and/or calculating of the acoustic impedance, as defined in step 1, of said at least one rock sample as a function of effective pressure and under in-situ fluid-saturation conditions;
(7b) computing the stiff and compliant porosity of said at least one rock sample as a function of effective pressure, said computing being carried out on the basis of a given analytical porosity model and the porosity of said at least one rock sample as a function of effective pressure as measured in step 4;
(8b) computing numerical coefficients of a given analytical permeability model based on the stiff and compliant porosities as determined in step 7 and on the permeability of said at least one rock sample as a function of effective pressure as measured in step 5,
(9b) computing coefficients of a given analytical model of an elastic-compliance characteristic of the rock based on the stiff and compliant porosity as determined in step 7 and on acoustic impedance of said at least one rock sample as a function of effective pressure as measured in step 6;
(10b) computing the stiff and compliant porosity for a plurality of other locations in said subsurface region based on the acoustic impedances in rocks in said subsurface region as measured in step 1, the stiff and compliant porosity as determined in step 7 and the coefficients determined in step 9; and
(11b) computing the permeability of rocks, which belong to said at least one lithological unit, for said at least one location in said subsurface region and for said plurality of other locations in said subsurface region, said computing being based on said stiff and compliant porosity of said at least one rock sample as a function of effective pressure as determined in step 7, the coefficients as determined in steps 8 and 9, and the stiff and compliant porosity for said plurality of other locations in said subsurface region as determined in step 10.

14. The method according to claim 13 wherein
a plurality of different lithological units are determined in step 2b,
for each of the plurality of different lithological units at least one rock sample is acquired and
steps 3b to 11b are carried out for each of said plurality of different lithological units and the permeability of rocks is computed for each of said plurality of different lithological units.

* * * * *